United States Patent [19]

Horn

[11] Patent Number: 4,540,691

[45] Date of Patent: Sep. 10, 1985

[54] DOPAMINE AGONISTS AND USE THEREOF

[75] Inventor: Alan S. Horn, Noordhorn, Netherlands

[73] Assignee: Nelson Research & Development Co., Irvine, Calif.

[21] Appl. No.: 600,008

[22] Filed: Apr. 13, 1984

[51] Int. Cl.³ .................. A61K 31/535; A61K 31/55; C07D 265/36; C07D 267/14
[52] U.S. Cl. .................. 514/211; 260/244.4; 260/330.3; 260/330.7; 260/243.3; 514/230; 514/232; 514/234; 514/236; 514/237; 514/239; 544/101; 544/73
[58] Field of Search .............. 544/101, 73; 260/244.4, 260/330.3, 330.7, 243.3; 424/244, 248.51, 248.52, 248.54, 248.55, 248.56, 248.58, 263, 275

[56] References Cited

U.S. PATENT DOCUMENTS 4,420,480 12/1983 Jones .............................. 424/248.4

OTHER PUBLICATIONS

Perrone, R. et al., Synthesis of Naphtho- and Indeno [1,4] Oxazines, A New Class of Rigid Dopamine Congeners, 1984, II Farmaco 39, 255.
Cannon, J. G., et al.; Rigid Congeners of Dopamine Based On Octahydrobenzo[f]quinoline: Pheripheral and Central Effects; Journal of Medicinal Chemistry, 1979, vol. 22, No. 4, 341-346.
Wikstrom, H., et al.; Monophenolic Octahydrobenzo[f]quinolines: Central Dopamine- and Serotonin-Receptor Stimulating Activity; J. Med. Chem. 1982, 25, 925-931.

Primary Examiner—Richard L. Raymond
Attorney, Agent, or Firm—Knobbe, Martens et al.

[57] ABSTRACT

Compounds are disclosed having the formula:

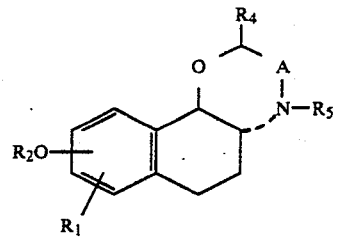

wherein: $R_1$ is H, OH, $-OCH_3$, $-CH_2OH$, $-NH_2$, $-NHMe$, $-NHEt$, $-NMe_2$, $-NEt_2$,

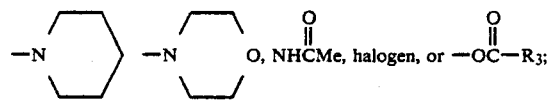

$R_2$ is H, $-CH_3$, or

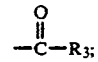

$R_3$ is phenyl, benzyl, or 1-4 carbon alkyl; $R_4$ is H, $-CH_3$, $-CH_2OH$, $-CH_2-CN$, $-CH_2-S-Me$, $CH_2-S-CN$, or

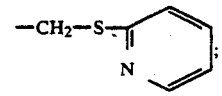

$R_5$ is H, 1-4 carbon alkyl, alkenyl, or alkynyl, or aralkyl having a 1-4 carbon alkylene moiety; and A is $-CH_2-$ or $-CH_2CH_2-$, and pharmaceutically-acceptable salts thereof. Pharmaceutical preparations using these compounds and a method for inducing a dopaminergic response by administering these compounds are also disclosed.

25 Claims, No Drawings

DOPAMINE AGONISTS AND USE THEREOF

BACKGROUND OF THE INVENTION

This invention relates to new substituted hexahydronaphthoxazines, pharmaceutical preparations containing such compounds as an active ingredient, and methods for using those compounds as pharmaceutical agents. More particularly, the invention relates to compounds having dopamine receptor agonist activity for therapeutic use in treating certain diseases of the central nervous system in mammals.

Compounds having dopaminergic activity have been the subject of extensive study in recent years, and a relatively large number of such compounds is known. The utility of L-DOPA in the symptomatic treatment of Parkinson's disease is well established and L-DOPA is in widespread clinical use. However, only a relatively small number of the other recognized dopaminergic agents have even been marketed. One of the major exceptions is Bromocriptine. Another promising compound has been Pergolide. However, most of the other compounds have not been commercialized because of a lack of pharmacological specificity; i.e., they have major and undesirable side effects.

One class of compounds that has excited a significant amount of activity in the field are the 9-oxaergolines. See, e.g., Anderson, et al., *J. Med. Chem.* 26, 363 (1983); Nedelec, et al., *J. Med. Chem.* 26, 522 (1983); Boissier, et al., *Eur. J. Pharmacol.*, 87, 183 (1983); Martin, et al., *Life Sci.*, 30, 1847 (1982).

The N-propyl-9-oxaergoline compound has been shown to be an extremely potent direct acting dopaminergic agonist, comparing favorably with pergolide.

N-PROPYL-9-OXAERGOLINE (RU 29717)

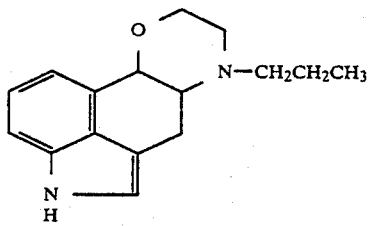

RU 29717 is an indolic compound, as are all the ergolines. The indole ring, without which the compound is inactive, is a significant limitation on the number and type of derivatives of the compound that may be prepared. Moreover, in addition to its potent dopaminergic properties, RU 29717 has adrenergic and serotonergic activity as well, giving the compound a relatively broad pharmacological profile. Its activity as an emetic is a significant problem.

The present invention is directed to a class of nonindolic dopamine receptor agonists. Surprisingly, these compounds are highly active dopaminergic agents, exhibiting dopaminergic properties comparable to RU 29717. At the same time, they are easily synthesized and have a structural flexibility which makes various phenols, catechols, and resorcinols readily available to replace the indole pharmacophore. Moreover, it is believed these compounds exhibit a much narrower pharmacological profile than RU 29717 and related compounds with the concomitant result of significantly fewer side effects and more specific action in pharmaceutical use.

SUMMARY OF THE INVENTION

The compounds of the invention have the formula:

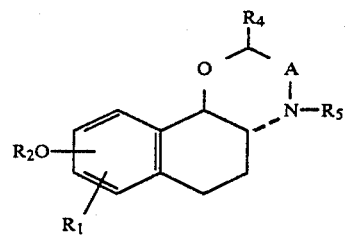

wherein: $R_1$ is H, OH, $-OCH_3$, $-CH_2OH$, $-NH_2$, $-NHMe$, $-NHEt$, $-NMe_2$, $NEt_2$,

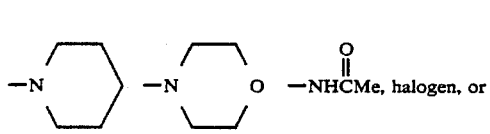

$-NHCMe$, halogen, or $$-O\overset{O}{\underset{\|}{C}}-R_3;\ R_2\ \text{is}$$

H, $-CH_3$, or

$R_3$ is phenyl, benzyl, or 1–4 carbon alkyl; $R_4$ is H, $-CH_3$, $-CH_2OH$, $-CH_2-CN$, $-CH_2-S-Me$, $-CH_2-S-CN$, or 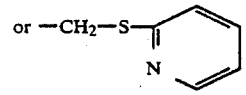

$R_5$ is H, 1–4 carbon alkyl, alkenyl, or alkynyl, or aralkyl having a 1–4 carbon alkylene group; and A is $-CH_2-$ or $-CH_2CH_2-$.

It will be understood that, for example, when A is $-CH_2-$, $R_1$ and $OR_2$ may be on any of numbered carbons 7, 8, 9, and 10. (The numbering scheme is based on $A = -CH_2-$.) When $R_1$ is H, no carbon need be specified. $R_1$ and $OR_2$ are substituted for hydrogens on the ring and do not destroy its aromatic character.

The compounds of the invention exhibit strong dopamine receptor agonist activity when administered to mammals. These compounds are thus useful, as demonstrated by standard animal tests, for the treatment of disorders of the central nervous system, especially those related to the dopaminergic systems, because they invoke a strong dopaminergic response in such tests.

The compounds of the invention may contain up to 3 asymmetric carbon atoms. The therapeutic properties of the compounds may to a greater or lesser degree be ascribed to any of the stereoisomers. Thus, the pure enantiomers of the cis and trans forms, as well as mixtures thereof, are within the scope of this invention.

In another embodiment of this invention, there are provided pharmaceutical compositions comprising the foregoing compounds in combination with an inert pharmaceutical carrier.

This invention also encompasses a method for inducing a dopaminergic response by administering the foregoing compounds to a patient.

In still another embodiment of the present invention, there are provided pharmaceutical compositions in dosage form containing a clinically effective amount of one of the foregoing dopaminergic compounds.

DETAILED DESCRIPTION OF THE PREFERRED EMBODIMENTS

The compounds of this invention may be prepared by the general method outlined below.

GENERAL SYNTHETIC METHOD

Most of the 5, 6, 7, and/or 8-methoxy-1-tetralones are known. See, e.g., Autrey & Scullard, *J. Am. Chem. Soc.* 90, 4924 (1968); Thomas and Nathan, *J. Am. Chem. Soc.* 70, 331 (1948); Thrift, *J. Chem. Soc. C.*, 288 (1967). The appropriate methoxy 1-tetralone (Compound 1) is reacted with n-butylnitrite and potassium ethoxide to yield the 2-hydroxyimino-1-tetralone (Compound 2). The latter is reduced over palladium-barium sulfate to give the 2-amino-1-tetralone (Compound 3).

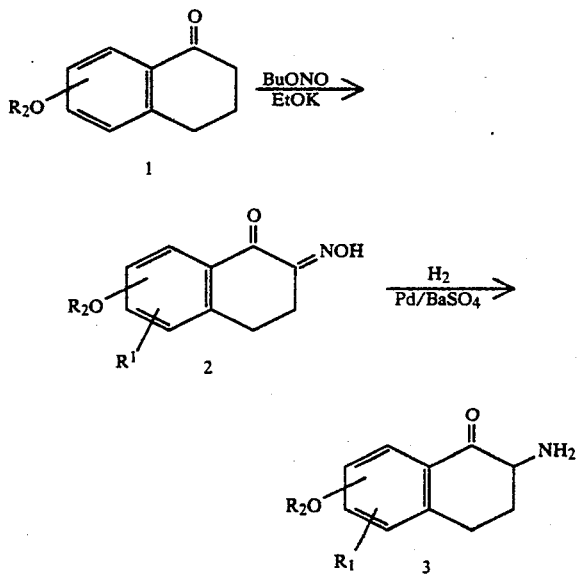

Reduction with sodium borohydride leads to the trans 2-amino-1 tetralol (Compound 4). Treatment of Compound 4 with chloroacetyl chloride or a suitably substituted derivative yields the chloroacetamide (Compound 5). (The size of the heterocyclic ring may be increased by substituting chloropropionyl chloride for chloroacetyl chloride.)

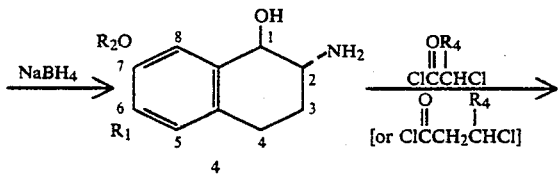

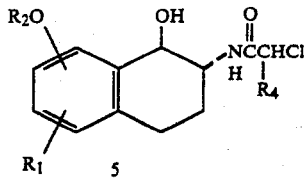

Reaction of (Compound 5) with sodium hydride or sodium hydroxide leads to ring closure to the lactam (Compound 6). Reduction of this lactam with lithium aluminum hydride gives the amine (Compound 7) in which A is $-CH_2-$.

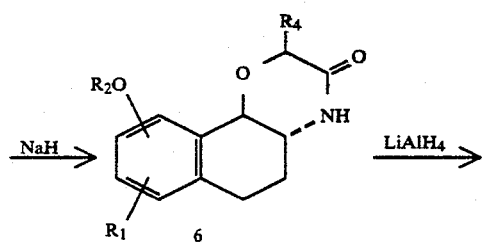

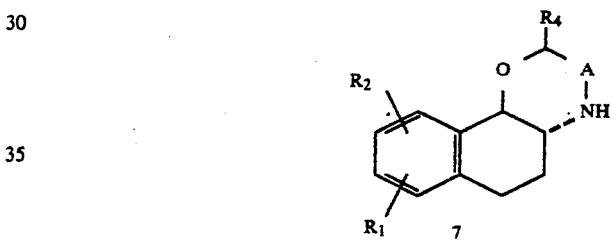

Alkylation with RI or RBr yields the tertiary amine (Compound 8). This can also be achieved by acylation of Compound 7 with an alkane carboxylic acid chloride followed by reduction with lithium aluminum hydride. ($R_5'$ is $R_5$ less one methylene unit.) A third alternative is to directly alkylate Compound 7 with a $NaBH_4$-carboxylic acid complex. On treatment with boron tribromide the methoxy group ($-OCH_3$) of Compound 8 is converted to a phenol ($-OH$) to yield Compound 9. (The numbering of the carbons corresponds to $A=-CH_2-$.)

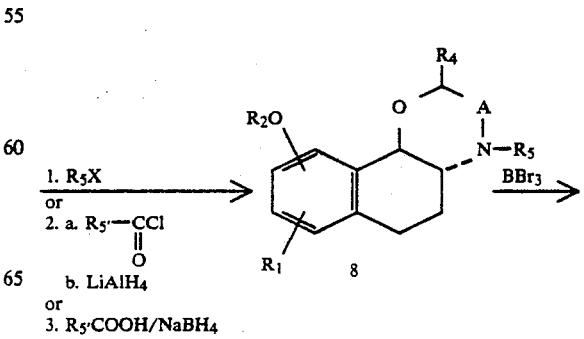

-continued

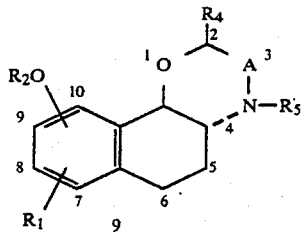

Prodrug esters of these compounds are prepared by reacting the phenols, resorcinols, or catechols with the desired corresponding acid chloride (Horn et al., J. Med. Chem. 25, 993, (1982)).

Details of this synthesis, together with modifications and variations specifically tailored for particular compounds, are set out more fully in the specific Examples which follow.

The preferred substituents for $R_1$ are H, OH, and

Preferred substituents for $R_2$ are H, $CH_3$, and

$R_3$ is preferably methyl, ethyl, t-butyl, or phenyl. It is further preferred that $R_4$ be H, $CH_2$—S—CN, or $CH_2SCH_3$. Preferred substituents for $R_5$ are methyl, ethyl, propyl, allyl, propargyl, cyclopropyl, phenylethyl, and 2- and 3-thienylethyl.

Certain particularly preferred compounds include N-N-propyl-9-hydroxy-2,3,4a,5,6,10b-hexahydro-4H-naphth-[1,2-b] [1,4] oxazine, N-ethyl-9-hydroxy-2,3,4a,5,6,10b-hexahydro-4H-naphth-[1,2-b] [1,4]oxazine, N-phenylethyl-9-hydroxy-2,3,4a,5,6,10b-hexahydro-4H-naphth-[1,2-b] [1,4]oxazine, N-2-thienylethyl-9-hydroxy-2,3,4a,5,6,10b-hexahydro-4H-naphth-[1,2-b] [1,4]oxazine, N-3-thienylethyl-9-hydroxy-2,3,4a,5,6,10b-hexahydro-4H-naphth-[1,2-b] [1,4]oxazine, and prodrug esters

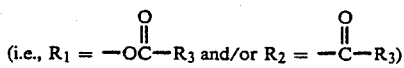

and pharmaceutically-acceptable salts thereof.

The substituents $R_1$ and $R_2$ are defined as including a large category of compounds, including various esters. The most pharmaceutically active form of the compounds of the invention is the hydroxy form. It will be understood, however, that the ester compounds (and to some extent the ether compounds) are prodrugs which are hydrolyzed in vivo by esterases to produce the active hydroxy form. For this reason, such hydrolyzable prodrug esters are deemed to be equivalents of the hydroxy compounds for purposes of this invention.

Accordingly, a wide range of ester and ether substituted compounds fall within the scope of the invention. Appropriate substituents may be selected by those of ordinary skill in the art on the basis of pharmaceutical considerations, such as palatability, and pharmacokinetic considerations, such as rapidity of hydrolysis to the active hydroxy form. Particularly preferred prodrug esters are the pivalates and benzoates.

PHARMACEUTICAL FORMULATION

The esters and acid addition salts of the compounds of the general formula are prepared in the conventional manner. As acid addition salts, the salts derived from a therapeutically acceptable acid such as hydrochloric acid, acetic acid, propionic acid and, more particularly, from a di- or poly- basic acid such as phosphoric acid, succinic acid, maleic acid, fumaric acid, citric acid, glutaric acid, citraconic acid, glutaconic acid, tartaric acid, malic acid, and ascorbic acid can be used.

A preferred embodiment of this invention is a method of treatment which comprises the administration of a therapeutically effective amount of the compounds of the above formula. In general the daily dose can be from 0.01 mg/kg to 10 mg/kg per day and preferably from 0.2 mg/kg to 4 mg/kg per day, bearing in mind, of course, that in selecting the appropriate dosage in any specific case, consideration must be given to the patient's weight, general health, metabolism, age and other factors which influence response to the drug.

In another embodiment of this invention there are provided pharmaceutical compositions in dosage unit form which comprise from about 1 mg to about 150 mg of a compound of the above formula, and preferably from about 5 mg to about 100 mg.

The pharmaceutical composition may be in any form suitable for oral use, such as tablets, aqueous or oily suspensions, dispersible powders or granules emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets may contain the active ingredient in admixture with non-toxic pharmaceutically acceptable excipients which are suitable for manufacture of tablets. These excipients may be inert diluents, for example calcium carbonate, sodium carbonate, lactose, calcium phosphate; granulating and disintegrating agents, such as corn starch, or alginic acid; binding agents, for example starch, gelatine or acacia; and lubricating agents, such as magnesium stearate, stearic acid or talc. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with an oil medium, for example arachis oil, liquid paraffin or olive oil.

The present invention also comprehends aqueous suspensions containing the active compound in admixture with suitable pharmacologically-acceptable excipients.

Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents such as a naturally-occurring phosphatide, for example lecithin, or condensation products of an alkylene oxide with fatty acids, for example polyoxythylene stearate, or condensation products of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, or n-propyl-p-hydroxy benzoate, one or more coloring agents, one or more flavoring agents, and one and more sweetening agents, such as sucrose, saccharin, aspartame, mannitol, sorbitol, or sodium or calcium cyclamate.

Dispersible powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative, and flavoring and coloring agents.

The pharmaceutical compositions may also be in the form of a sterile injectable preparation, for example as a sterile injectable aqueous suspension. This suspension may be formulated as is conventional using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol.

The pharmaceutical compositions may be tabulated or otherwise formulated so that for every 100 parts by weight of the composition there are present between 5 and 95 parts by weight of the active ingredient and preferably between 25 and 85 parts by weight of the active ingredient. The dosage unit form for humans will generally contain between about 1 mg and about 100 mg of the active ingredient of the formula stated above.

From the foregoing formulation discussion it is apparent that the compositions of this invention can be administered orally or parenterally. The term parenteral as used herein includes subcutaneous injection, intravenous, intramuscular, or intrasternal injection or infusion techniques.

The following Examples illustrate the present invention. Parenthetical reference will be made to the corresponding compounds of the general synthesis, together with reference to the identity and position of the R groups.

Example 1 illustrates the synthesis of a compound of the invention where $R_2$ is methyl and $R_5$ is propyl.

EXAMPLE 1

Preparation of N-n-propyl-9-methoxy 2,3,4a,5,6,10b-hexahydro-4H-naphth-[1,2-b][1,4]oxazine The known compound 2-hydroximino-7-methoxy-1-tetralone (Compound 2, $R_1=H$, $R_2=Me$ on C7) was prepared according to the method of Chiemprasert et al., 1965 Liebigs Ann. Chem. 685, 141–148. The yield was 50%. 9.9 g of this compound was dissolved in a mixture of 250 ml of methanol and 40 ml of 2N HCl. 1.5 g of Pd-BaSO$_4$ was added and the mixture was reduced in a Parr apparatus at room temperature under a hydrogen pressure of 0.9 atmospheres until the theoretical amount of hydrogen had been absorbed. The mixture was then filtered and the solvents were removed under reduced pressure. The resulting crude product was recrystallized from methanol-ether to yield a HCl salt [8.5 g, 77% yield, m.p. 234°–235°] of the known amino ketone (Compound 3, $R_1=H$, $R_2=Me$ on C7). This compound has been previously prepared by another method. See Chiemprasert et al., 1965.

This amino ketone was reduced to the known trans-2-amino-7-methoxy-1-tetralol (Compound 4, $R_1=H$, $R_2=Me$ on C7) with sodium borohydride according to the method of Chiemprasert et al., 1965. The yield was 78%.

To 3.4 g of this amino alcohol dissolved in 180 ml chloroform, a solution of 4.3 g of sodium hydroxide in 35 ml water was added. 3.38 g of chloroacetylchloride was then added dropwise. This mixture was stirred for 2 hr. at room temperature. The reaction mixture was then poured into 200 ml of water. The separated aqueous layer was extracted with dichloromethane (3×50 ml) and then combined with the chloroform layer. The organic extracts were washed with water (2×50 ml) and then dried over anhydrous magnesium sulfate. Removal of the organic solvents under reduced pressure yielded 3.1 g (78%) of the chloroacetamide (Compound 5, $R_1=H$, $R_2=Me$ on C7, $R_4=H$). Recrystallization from ethyl acetate produced white crystals m.p. 166°–167° C.

700 mg of the chloroacetamide (Compound 5) was dissolved in 125 ml of dimethoxyethane (DME) and added dropwise to 400 mg of sodium hydride (55% in oil) in 25 ml DME. The reaction mixture was stirred for 2.5 hr at room temperature. It was then poured into 200 ml of water and extracted with dichloromethane (3×25 ml). The organic layer was separated, shaken with water, dried over magnesium sulfate and then evaporated to dryness. Recrystallization from acetone-hexane gave the lactam (Compound 6, $R_1=H$, $R_2=Me$ on C9, $R_4=H$) as a white solid, 480 mg (79%) m.p. 218°–221° C.

The lactam (Compound 6) (470 mg) was dissolved in 50 ml of tetrahydrofuran (THF) and 380 mg LiAlH$_4$ was added. The mixture was refluxed for 3 hr. under a nitrogen atmosphere. The excess LiAlH$_4$ was destroyed by careful addition of 0.4 ml water followed by 0.4 ml 4N sodium hydroxide solution and a further 1.2 ml water. The mixture was filtered and the solid washed with ether. The organic filtrate was dried over magnesium sulfate. Removal of the solvent gave an oil. This was dissolved in dry ether and ether-HCl was added dropwise to produce the amine (Compound 7, $R_2=Me$ on C9, $R_4=H$, $A=-CH_2-$) as a white solid, 480 mg (93%) m.p. 235°–237° C.

450 mg of this amine, 800 mg of potassium carbonate, and 1.7 g of n-propyliodide were dissolved in 50 ml of DMF. The solution was stirred for 2 hr at 55° C. and then poured into 200 ml of water and extracted with ether (4×50 ml). The organic layer was separated and washed with a saturated solution of sodium chloride (3×10 ml) and once with a 10% ammonium chloride solution (10 ml). The ether layer was then dried and evaporated to dryness to yield an oil which was converted to a HCl salt of the amine (Compound 8, $R_1=H$, $R_2=Me$ on C9, $R_4=H$, $R_5=$n-propyl, $A=-CH_2-$); 346 mg (66%); m.p. 214°-217° C.

Example 2 illustrates the conversion of the methoxy compound into the active hydroxy compound.

EXAMPLE 2

Preparation of N-n-propyl-9-hydroxy-2,3,4a,5,6,10b-hexahydro-4H-naphth-[1,2-b] [1,4]oxazine 500 mg of Compound 8 from Example 1 were dissolved in 35 ml of $CH_2Cl_2$ and the temperature of the solution was lowered to $-60°$ C. with a dry ice/acetone bath. 2 ml of 1 mol. solution of $BBr_3$ in $CH_2Cl_2$ was then added and the reaction mixture was stirred for 2 hr. at a temperature between $-30°$ and $-40°$ C. The temperature was then allowed to rise and the mixture was stirred for a further 20 hr. at room temperature. The reaction mixture was then poured into water (100 ml) made alkaline by the addition of dilute sodium bicarbonate solution and then extracted with ether (5×50 ml). The combined ether extracts were washed with saturated saline (3×10 ml) and dried over $MgSO_4$. Removal of the ether under reduced pressure yielded a semi-solid white product. Conversion to a HCl salt gave 450 mg of crude product. Recrystallization from ethanol yielded 310 mg (65%) of pure product, Compound 9, ($R_1=H$, $R_2=OH$ on C9, $R_4=H$, $R_5=H$, n-propyl, $A=-CH_2-$), m.p. 244°-247° C. The structures of all new compounds were established with the help of I.R. and N.M.R. spectroscopy, mass spectrometry and elemental analysis.

Example 3 illustrates the preparation of the 8,9-dimethoxy compound in which $R_1$ is $OCH_3$ on C8 and $R_2$ is $CH_3$ on C9.

EXAMPLE 3

Preparation of N-n-propyl-8,9-dimethoxy-2,3,4a,5,610b-hexahydro-4H-naphth-[1,2-b] [1,4] oxazine The known compound 2-hydroxyimino-6,7-dimethoxy-1tetralone is prepared according to the method of Thrift, *J. Chem. Soc. C,* 288 (1967). (Compound 2, $R_1=OMe$ on C6, $R_2=Me$ on C7.) The synthesis then proceeds according to Example 1 to form Comlpound 8, N-n-propyl-8,9-dimethoxy-2,3,4a,5,6,10b-hexahydro-4H-naphth-[1,2b][1,4] oxazine.

Example 4 illustrates the preparation of the 8,9-dihydroxy compound from the compound of Example 3.

EXAMPLE 4

Preparation of N-n-propyl-8,9-dihydroxy-2,3,4a, 5,6,10b-hexahydro-4H-naphth-[1,2,-b][1,4] oxazine The compound of Example 3 is converted into the 8,9-dihydroxy compound (Compound 9, $R_1=OH$ on C8, $R_2=H$ on C9, $R_4=H$, $R_5=$n-propyl and $A=-CH_2-$) in accordance with Example 2.

Example 5 demonstrates how any desired prodrug ester may be prepared from the corresponding hydroxy compound.

EXXAMPLE 5

Preparation of a prodrug ester

The benzoate of the compound of Example 2 is prepared by reacting the hydroxy Compound 9 with benzoyl chloride. See Horn et al., *J. Med. Chem.* 25, 993 (1982).

Examples 6-10 illustrate the method by which substituent $R_5$ is selected by reacting Compound 7 with the appropriate hydrocarbon halide or acid.

EXAMPLE 6

Synthesis of N-ethyl-9-hydroxy-2,3,4a, 5,6,10b-hexahydro-4H-naphth-[1,2,-b] [1,4] oxazine The synthesis proceeds in accordance with Examples 1 and 2, with the exception that Compound 7 is reacted with ethyliodide instead of n-propyliodide.

EXAMPLE 7

Synthesis of N-propargyl-9-methoxy-2,3,4a,5,6,10b-hexahydro-4H-naphth-[1,2-b] [1,4] oxazine The synthesis proceeds in accordance with Example 1, with the exception that Compound 7 is reacted with propargyl bromide instead of n-propyliodide.

EXAMPLE 8

Synthesis of N-phenylethyl-9-hydroxy-2,3,4a,5,6,10b-hexahydro-4H-naphth-[1,2-b][1,4] oxazine The synthesis proceeds in accordance with Example 1 with the exception that Compound 7 is reacted with phenylacetic acid and $NaBH_4$ instead of n-propyliodide, as follows:

$NaBH_4$ is added portionwise to a stirred solution of phenylacetic acid. The amine (Compound 7, $R_2=Me$ on C9, $R_4=H$, $A=-CH_2-$) is added, and the mixture is refluxed and then treated with NaOH. The organic layer is dried with $Na_2SO_4$, and the solvent is evaporated. The residue is then converted to the HCl amine (Compound 8, $R_1=H$, $R_2=Me$ on C9, $R_4=H$, $R_5=$phenylethyl, and $A=-CH_2-$). See Hacksell et al., *J. Med. Chem.* 22, 1469 (1979). The synthesis then proceeds in accordance with Example 2 to yield the desired compound.

EXAMPLE 9

Synthesis of N-2-thienylethyl-9-hydroxy-2,3,4a,5,6, 10b-hexahydro-4H-naphth-[1,2-b][1,4] oxazine The synthesis proceeds in accordance with Example 8 with the exception that Compound 7 is reacted with 2-thienylacetic acid instead of phenylacetic acid.

EXAMPLE 10

Synthesis of N-3-thienylethyl-9-hydroxy-2,3,4a,5,6, 10b-hexahydro-4H-naphth-[1,2-b][1,4] oxazine The syntehsis proceeds in accordance with Example 8 with the exception that Compound 7 is reacted with 3-thienylacetic acid instead of phenylacetic acid.

Example 11 illustrates the manner in which $R_4$ substituents are placed on carbon 2.

EXAMPLE 11

Preparation of N-n-propyl-2-methyl-9-methoxy-2,3,4a,5,6, 10b-hexahydro-4H-naphth[1,2-b][1,4] oxazine The synthesis proceeds according to Example 1, except that Compound 4 is reacted with b-chloropropionyl chloride instead of chloroacetylchloride.

Examples 12–14 demonstrate another method for introducing $R_4$ substituents on carbon 2.

EXAMPLE 12

Preparation of 2-cyanomethyl-9-methoxy-2,3,4a,5,6,10b-hexahydro-4H-naphth-[1,2-b][1,4] oxazine.

The synthesis of Example 1 proceeds through preparation of Compound 4 ($R_2$=Me on C7). Compound 4 is then reacted with an excess of epichlorhydrin and distilled under reduced pressure to yield Compound 10.

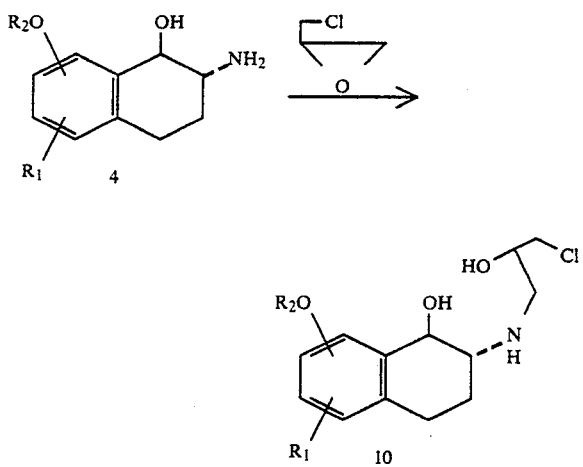

Compound 10 is dissolved in 98% $H_2SO_4$ and heated to 150° C. for 30 minutes to effect ring closure by dehydration. The resulting solution is cooled, added to ice and NaOH, and extracted with toluene. Concentration and recrystallization yields the 2-chloromethyl Compound 11 ($R_4$=$CH_2Cl$). Treatment with potassium cyanide produces the desired compound. (Compound 12, $R_1$=H, $R_2$=$CH_3$ on C9, $R_4$=$CH_2CN$, $R_5$=H.) If necessary, an alkali metal iodide in stoichiometric amounts may be used to accelerate the reaction and improve the yield.

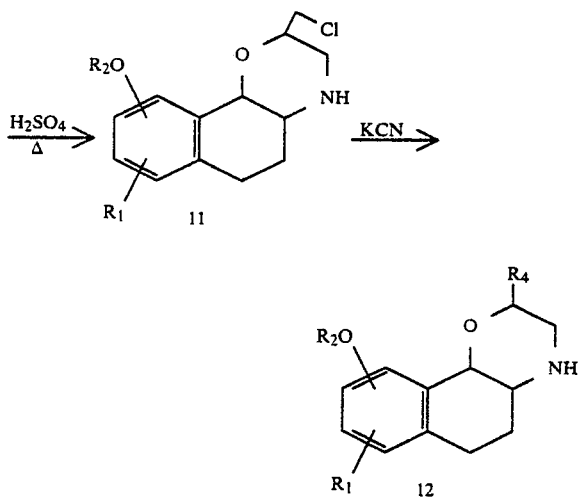

EXAMPLE 13

Preparation of 2-(Methylthio)methyl-9-methoxy-2,3,4a,5,6,10b-hexahydro-4H-naphth-[1,2-b] [1,4] oxazine The synthesis proceeds according to Example 12, except Compound 11 is reacted with sodium thiomethoxide instead of potassium cyanide to form the desired 2-(methylthio)methyl compound ($R_1$=H, $R_2$=$CH_3$ on C9, $R_4$=$CH_2SCH_3$, $R_5$=H).

EXAMPLE 14

Preparation of 2-hydroxymethyl-9-methoxy-2,3,4a5,6,10b-hexahydro-4H-naphth-[1,2-b] [1,4] oxazine Compound 11 is added to a solution of 10% molar excess of water in formamide and the resulting mixture is heated under reflux for 3 hours. The resulting solution is cooled and another 10% molar excess of water is added. The solution is further refluxed for 2 hours, cooled to room temperature and diluted with water. The resulting solution is made strongly basic (pH 12) with aqueous sodium hydroxide solution and the basic solution is extracted with an organic solvent, dried over $MgSo_4$ and concentrated to give the hydroxymethyl compound. The pure compound is obtained by recrystallization. ($R_1$=H, $R_2$=$CH_3$ on C9, $R_4$=$CH_2OH$, $R_5$=H)

The manner in which an $R_5$ substituent may be added to Compound 12 for increased dopaminergic activity is demonstrated in Example 15.

EXAMPLE 15

Preparation of N-n-propyl-2(methylthio)methyl-9-methoxy-2,3,4a,5,6,10b-hexahydro-4H-naphth-[1,2-b][1,4] oxazine The compound of Example 13 is reacted with 1-bromopropane in the presence of a base such as diisopropylethylamine to form the N-n-propyl Compound 8 ($R_1$=H, $R_2$=$CH_3$ on C9, $R_4$=$CH_2$-$SCH_3$, $R_5$=n-propyl).

To the extent that appropriately substituted tetralones (Compound 1) or 2-hydroxyimino-1-tetralones (Compound 2) are not available, they may be synthesized, e.g., from a substituted 4-phenylbutanoic acid in accordance with Examples 16 and 17.

EXAMPLE 16

Synthesis of substituted tetralones 4-(p-methoxyphenyl)butanoic acid (Compound 13, $R_1$=H, $R_2$=$CH_3$) is treated with polyphosphoric acid (PPA) to form 7-methoxytetralone via Friedel-Crafts acylation (Compound 1, $R_1$=H, $R_2$=$CH_3$ on C7.

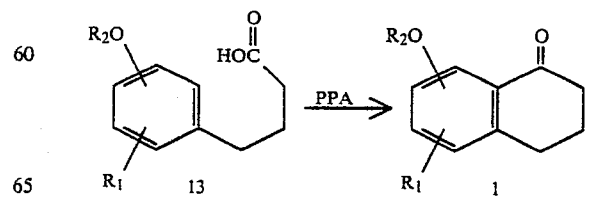

The tetralone (Compound 1) is then reacted with N-butylnitrite and potassium ethoxide to yield 2-hydroxyimino-7-methoxy-1-tetralone (Compound 2, $R_2=CH_3$ on C7.

EXAMPLE 17

Synthesis of disubstituted tetralones 4-(o-dimethylamino-p-methoxyphenyl)butanoic acid is cyclized with PPA as in Example 15 to yield 5-dimethyl amino-7-methoxytetralone (Compound 1, $R_1=N(CH_3)_2$ on C5, $R_2=CH_3$ on C7).
The method by which the oxazine ring is enlarged to a seven-member ring is illustrated in Example 18.

EXAMPLE 18

Enlargement of the heterocyclic ring

The synthesis proceeds according to Example 1, with the exception that Compound 4 is reacted with β-chloropropionyl chloride instead of chloroacetyl chloride. The resulting compound has a seven-member heterocyclic ring (Compound 7, $A=-CH_2CH_2-$).

PHARAMACOLOGICAL ACTIVITY OF CERTAIN ANALOGUES

The dopaminergic activity of three analogues (A,B,C) was evaluated in comparison with the indolic structural analogue RU 29717 (Nedelec et al., 1983, J. Med. Chem., 26, 522) in three test systems. Compounds B and C are within the scope of the present invention. Compound A, a novel compound having an unsubstituted aromatic ring, is included for comparison to demonstrate the effect of aromatic ring substituents on activity.

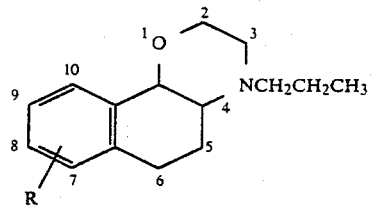

A: R = H
B: R — OH on C7
C: R = OH on C9

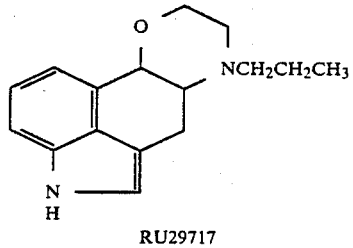

RU29717

EXAMPLE 19

Radioligand binding assay

The ability of the above compounds to displace the specific binding of $^3H$-5,6-dihydroxy-N,N-dipropyl-2-aminotetralin, a potent DA receptor agonist (Feenstra et al., Life Sci., 32, 1313 (1983)) to homogenates of rat corpus striatum was studied.

METHOD

The assay was performed essentially according to the method of Leysen and Gommeran J. Neurochem. 36, 201 (1981) for $^3H$-apomorphine binding.

| Results | |
|---|---|
| Compound | $IC_{50}$(nM) |
| RU 29717 | 3.0 |
| A | 110.0 |
| B | 80.0 |
| C | 2.8 |
| Apomorphine | 3.2 |

The $IC_{50}$ is the concentration of drug required to inhibit the specific binding by 50%. The results are presented as the mean values of 3 independent experiments each analyzed in triplicate over the concentration range $10^{-11}$ to $10^{-5}M$.

CONCLUSION

Compound C has a similar potency to RU 29717 and apomorphine. Compound B has some activity, and the least potent is compound A.

EXAMPLE 20

Effect on dopamine metabolism

Dopamine agonists are known to produce a lowering of the striatal levels of one of the main metabolites of dopamine, homovanillic acid, HVA, (Feenstra et al., 1983 Arch. Pharmacol., 324, 108).

METHOD

Female Wistar rats (160–180g) were injected with the drugs under test dissolved in saline and were then decapitated 60 min later. The HVA content of the corpus striatum was determined according to the method of Westerink and Mulder (J. Neurochem., 1981 36, 1449).

| | Results | |
|---|---|---|
| Compound-dose | HVA (μg/g) | % control |
| Control | 0.98 ± 0.08 (5) | 100 ± 8.2 |
| RU 29717, 0.2 μmol/kg | 0.50 ± 0.04 (4)** | 51.0 ± 4.1 |
| RU 29717, 0.4 μmol/kg | 0.46 ± 0.02 (4)** | 46.9 ± 2.0 |
| A, 0.4 μmol/kg | 0.90 ± 0.02 (4) | 91.8 ± 2.0 |
| B, 0.4 μmol/kg | 0.96 ± 0.12 (4) | 98.0 ± 12.2 |
| C, 0.2 μmol/kg | 0.62 ± 0.04 (4)* | 63.3 ± 4.1 |
| C, 0.4 μmol/kg | 0.47 ± 0.01 (4) | 48.0 ± 1.0 |

Values are presented as means ± S.E.M. with the number of determinations in parenthesis.
*$p < 0.05$,
**$p < 0.01$, Dunnett's t-test.

CONCLUSIONS

Compound C is comparable in activity to RU 29717.

EXAMPLE 21

Presynaptic DA activity in the GBL model.

The ability of a dopamine agonist to counteract the gamma-butyrolactone (GBL) induced rise in DOPA levels in the rat striatum is an indication of its activity at presynaptic dopamine receptors. (Walters and Roth, 1976 Arch. Pharmacol., 296, 5).

METHOD

The experiments were performed in rats according to the method of Walters and Roth (ibid). The striatal levels of DOPA were determined using the method of Westerink and Mulder (1981 J. Neurochem. 36, 1449). NSD 1015 was used as decarboxylase inhibitor.

Results

| Compound | DOPA (µg/g) | % Reversal vs. GBL group |
|---|---|---|
| NSD 1015 | 1.89 ± 0.09 (5) | 100 |
| GBL + NSD 1015 | 5.41 ± 0.46 (5) | 0 |
| RU 29717, 0.2 µmol/kg | 2.30 ± 0.16 (4) | 88.4* |
| A, 0.2 µmol/kg | 5.25 ± 0.09 (4) | 4.5 |
| B, 0.2 µmol/kg | 4.80 ± 0.37 (4) | 17.3 |
| C, 0.2 µmol/kg | 2.08 ± 0.12 (4) | 94.6* |

*$p < 0.01$, Dunnett's t-test.

CONCLUSION

Compound C appears to be slightly more potent than RU 29717 in this test system.

GENERAL CONCLUSION

Compounds B and C both exhibit useful levels of dopamine agonist activity. Compound C appears to be as active as the known DA agonist RU 29717 in various tests which evaluate pre- and post-synaptic dopaminergic activity. Compound A, lacking an R substituent on the aromatic ring, was significantly less active.

What is claimed is:

1. A compound of the formula:

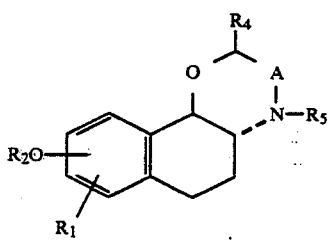

wherein: $R_1$ is H, OH, —OCH$_3$, —CH$_2$OH, —NH$_2$, —NHMe, —NHEt, —NMe$_2$, —NEt$_2$,

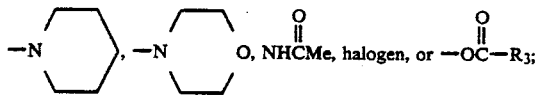

$R_2$ is H, —CH$_3$, or

$R_3$ is phenyl, benzyl, or 1-4 carbon alkyl; $R_4$ is —CH$_2$OH, —CH$_2$—CN, —CH$_2$—S—Me, —CH$_2$—S—CN, or

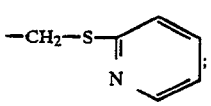

$R_5$ is H, 1-4 carbon alkyl, alkenyl, or alkynyl, or aralkyl having a 1-4 carbon alkylene moiety; and A is —CH$_2$— or —CH$_2$CH$_2$—;

or a pharmaceutically-acceptable salt thereof.

2. The compound of claim 1, wherein $R_1$ is H, OH, or

$R_2$ is H or

$R_3$ is methyl, ethyl, t-butyl, or phenyl; $R_4$ is —CH$_2$-S-CN, or CH$_2$-S-CH$_3$; $R_5$ is methyl, ethyl, propyl, allyl, propargyl, cyclopropyl, phenylethyl, 2-thienylethyl or 3-thienylethyl; and A is —CH$_2$—.

3. The compound of claim 2, wherein $R_5$ is 2-thienylethyl or 3-thienylethyl.

4. The compound of claim 1, wherein $R_5$ is propargyl.

5. The compound of claim 3, wherein $R_1$ is OH and $R_2$ is H.

6. The compound of claim 5, wherein $R_1$ is on C7 and $R_2$O- is on C8.

7. The compound of claim 5, wherein $R_1$ is on C8 and $R_2$O- is on C9.

8. The compound of claim 3, wherein $R_1$ is H and $R_2$ is H.

9. The compound of claim 8, wherein $R_2$O- is on C9.

10. The compound of claim 3, wherein $R_1$ is H, $R_2$ is

and $R_3$ is phenyl or t-butyl.

11. The compound of claim 2, wherein $R_4$ is —CH$_2$-S-CN.

12. The compound of claim 2, wherein $R_4$ is —CH$_2$-S-CH$_3$.

13. A compound of the formula:

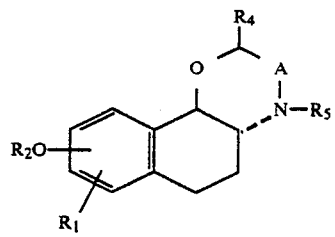

wherein: $R_1$ is H, OH, —OCH$_3$, —CH$_2$OH, —NH$_2$, —NHMe, —NHEt, —NMe$_2$, —NEt$_2$,

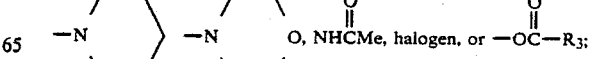

$R_2$ is H, —CH$_3$, or

R3 is phenyl, benzyl, or 1-14 carbon alkyl; R4 is H, —CH3, —CH2OH, —CH2-CN, —CH2-S-Me, —CH2-S-CN, or

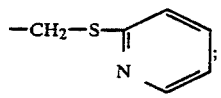

R5 is 2-thienylethyl, or 3-thienylethyl; and A is —CH2— or —CH2CH2—; or a pharmaceutically-acceptable salt thereof.

14. The compound of claim 13, wherein $R_1$ is H, OH, or

$R_2$ is H or

$R_3$ is methyl, ethyl, t-butyl, or phenyl; and $R_4$ is H, —CH2-S-CN, or CH2-S-CH3.

15. N-2-thienylethyl-9-hydroxy-2,3,4a,5,6,10b-hexahydro-4H-naphth-[1,2-b][1,4] oxazine or a pharmaceutically acceptable salt thereof.

16. N-3-thienylethyl-9-hydroxy-2,3,4a,5,6,10b-hexahydro-4H-naphth-[1,2-b][1,4] oxazine or a pharmaceutically acceptable salt thereof.

17. A pharmaceutical composition, comprising: an active ingredient of the formula

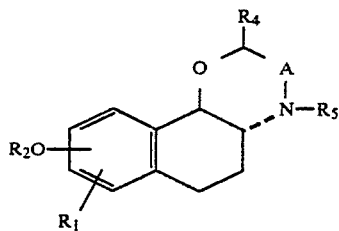

wherein: $R_1$ is H, OH, —OCH3, —CH2OH, —NH2, —NHMe, —NHEt, —NMe2, —NEt2,

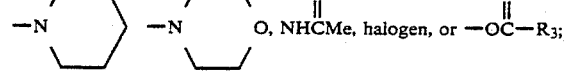

$R_2$ is H, —CH3, or

$R_3$ is phenyl, benzyl, or 1-4 carbon alkyl; $R_4$ is —CH2OH, —CH2-CN, —CH2-S-Me, CH2-S-CN, or

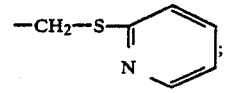

$R_5$ is H, 1-4 carbon alkyl, alkenyl, or alkynyl, or aralkyl having a 1-4 carbon alkylene moiety; and A is —CH2— or —CH2CH2—, or a pharmaceutically-acceptable salt thereof; and
    a pharmaceutically-acceptable carrier.

18. The composition of claim 17, wherein, in said active ingredient, $R_1$ is H, OH, or

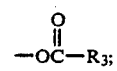

$R_2$ is H or

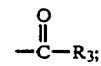

$R_3$ is methyl, ethyl, t-butyl, or phenyl; $R_4$ is —CH2-S-Cn, or CH2-S-CH3; $R_5$ is methyl, ethyl, propyl, allyl, propargyl, cyclopropyl, phenylethyl, 2-thienylethyl or 3-thienylethyl; and A is —CH2—.

19. A pharmaceutical composition, comprising: an active ingredient of the formula

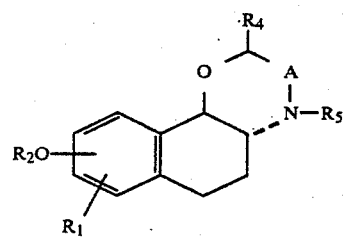

wherein: $R_1$ is H, OH, —OCH3, —CH2OH, —NH2, —NHMe, —NHEt, —NMe2, —NEt2,

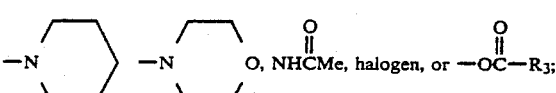

$R_2$ is H, —CH3, or

$R_3$ is phenyl, benzyl, or 1-4 carbon alkyl; $R_4$ is H, —CH3, —CH2OH, —CH2-CN, —CH2-S-Me, CH2-S-CN, or

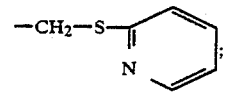

$R_5$ is 2-thienylethyl, or 3-thienylethyl; and A is —CH2— or —CH2CH2—; or a pharmaceutically-acceptable salt thereof; and a pharmaceutically-acceptable carrier.

20. The composition of claim 19, wherein, in said active ingredient, R₁ is H, OH, or

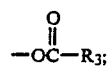

R₂ is H or

R₃ is methyl, ethyl, t-butyl, or phenyl; and R₄ is H, —CH₂-S-CN, or CH₂-S-CH₃.

21. The composition of claim 19, wherein said active ingredient is N-2-thienylethyl-9-hydroxy-2,3,4a,5,6,10b-hexahydro-4H-naphth-[1,2-b][1,4] oxazine or a pharmaceutically acceptable salt or a prodrug ester thereof.

22. The composition of claim 19, wherein said active ingredient is N-3-thienylethyl-9-hydroxy-2,3,4a,5,6,10b-hexahydro-4H-naphth-[1,2-b][1,4] oxazine or a pharmaceutically acceptable salt or a prodrug ester thereof.

23. A method for inducing a dopaminergic response, comprising the step of administering to a patient a dopaminergically-effective amount of a compound having the formula:

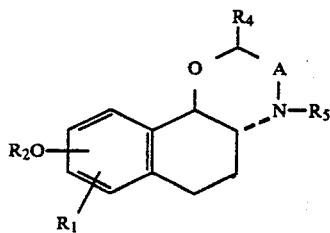

wherein: R₁ is H, OH, —OCH₃, —CH₂OH, —NH₂, —NHMe, —NHEt, —NMe₂, —NEt₂,

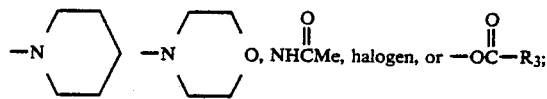

R₂ is H, —CH₃, or

R₃ is phenyl, benzyl, or 1-4 carbon alkyl; R₄ is —CH₂OH, —CH₂-CN, —CH₂-CN, —CH₂-S-Me, CH₂-S-CN, or

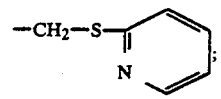

R₅ is H, 1-4 carbon alkyl, alkenyl, or alkynyl, or aralkyl having a 1-4 carbon alkylene moiety; and A is —CH₂— or —CH₂CH₂—, and pharmaceutically-acceptable salts thereof.

24. The method of claim 23, wherein in said compound, R₁ is H, OH, or —OC-R₃; R₂ is H or —C-R₃; R₃ is methyl, ethyl, t-butyl, or phenyl; R₄ is —CH₂-S-CN, or CH₂-S-CH₃; R₅ is methyl, ethyl, propyl, allyl, propargyl, cyclopropyl, phenylethyl, 2-thienylethyl or 3-thienylethyl; and A is —CH₂—.

25. A method for inducing a dopaminergic response, comprising the step of administering to a patient a dopaminergically-effective amount of a compound having the formula:

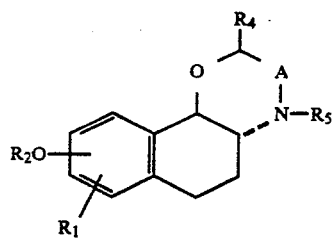

wherein: R₁ is H, OH, —OCH₃, —CH₂OH, —NH₂, —NHMe, —NHEt, —NMe₂, —NEt₂,

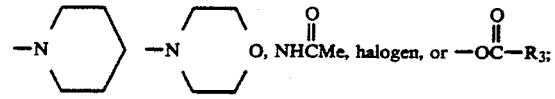

R₂ is H, —CH₃, or

R₃ is phenyl, benzyl, or 1-4 carbon alkyl; R₄ is H, —CH₃, —CH₂OH, —CH₂-CN, —CH₂-S-Me, CH₂-S-CN, or

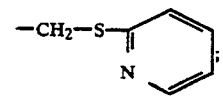

R₅ is 2-thienylethyl, or 3-thienylethyl; and A is —CH₂— or —CH₂CH₂—; or a pharmaceutically-acceptable salt thereof.

* * * * *